(12) United States Patent
Gross

(10) Patent No.: US 6,745,630 B2
(45) Date of Patent: Jun. 8, 2004

(54) METHOD AND DEVICE FOR DETECTING STENOSES IN A TUBULAR LINE SYSTEM

(75) Inventor: Malte Gross, Schweinfurt (DE)

(73) Assignee: Fresenius Medical Care Deutschland, Bad Homburg (DE)

( * ) Notice: Subject to any disclaimer, the term of this patent is extended or adjusted under 35 U.S.C. 154(b) by 0 days.

(21) Appl. No.: 10/112,522

(22) Filed: Mar. 29, 2002

(65) Prior Publication Data
US 2002/0174721 A1 Nov. 28, 2002

(30) Foreign Application Priority Data
Mar. 30, 2001 (DE) .......................... 101 15 991

(51) Int. Cl.[7] .......................... G01N 29/00; A61B 5/02; A61M 37/00
(52) U.S. Cl. .......................... 73/592; 73/659; 600/485; 600/486; 604/4.01; 604/27; 604/31
(58) Field of Search .............................. 604/4.01, 6.16, 604/6.06, 6.12; 600/485, 486

(56) References Cited

U.S. PATENT DOCUMENTS

| 4,969,470 A | | 11/1990 | Mohl et al. ........... 600/486 |
|---|---|---|---|
| 6,033,357 A | * | 3/2000 | Ciezki et al. ........... 600/3 |
| 6,090,048 A | * | 7/2000 | Hertz et al. ........... 600/485 |
| 6,328,698 B1 | * | 12/2001 | Matsumoto ........... 600/481 |
| 6,416,492 B1 | * | 7/2002 | Nielson ........... 604/22 |

FOREIGN PATENT DOCUMENTS

| DE | 199 01 078 | 2/2000 |
|---|---|---|
| EP | 099 5451 | 4/2000 |
| EP | 104 4695 | 10/2000 |
| WO | WO 97/10013 | 3/1997 |

* cited by examiner

Primary Examiner—Hezron Williams
Assistant Examiner—Jacques Saint-Surin
(74) Attorney, Agent, or Firm—Kenyon & Kenyon

(57) ABSTRACT

A method and device for detecting stenoses in a tubular line system during an extracorporeal hemotherapy. The tubular line system has an arterial branch going out from the patient and leading to a hemotherapeutic unit, and a venous branch going out from the hemotherapeutic unit and leading to the patient, where an oscillating pressure signal is generated in the tubular line system, and the oscillating pressure signal is measured. To detect stenoses, the frequency spectrum of the oscillating pressure signal is analyzed, in response to a change in the frequency spectrum. This method is based on the principle that, in response to the existence of a stenosis, the dynamic performance of the tubular line system changes, the higher frequency components of the pressure signal generated by the rollers of the blood pump, which propagates across the tubular line system, being attenuated due to the compliance of the line system.

18 Claims, 3 Drawing Sheets

METHOD AND DEVICE FOR DETECTING STENOSES IN A TUBULAR LINE SYSTEM

FIELD OF THE INVENTION

The present invention is directed to a method and a device for detecting stenoses in a tubular line system during an extracorporeal hemotherapy.

BACKGROUND OF THE INVENTION

Extracorporeal hemotherapy is a standard procedure today which is used, above all, for treating renal insufficiency in the form of hemodialysis, hemofiltration, or hemodiafiltration. An extracorporeal hemotherapy requires effective access to the patient's circulatory system. For some years now, to access the patient's blood, it has proven effective to position a shunt underneath the skin, between an artery and a vein. During extracorporeal hemotherapy, the patient's blood flows via the arterial branch of the tubular line system into the hemotherapeutic unit, for example into a hemodialyzer or hemofilter, and from the hemotherapeutic unit via the venous branch of the line system back to the patient. The blood is delivered by a volumetric blood pump, in particular a roller pump positioned in the arterial branch of the line system. The known protection systems generally monitor the pressure of the blood, both in the arterial branch, as well as in the venous branch of the line system. To accomplish this, provision is made for an arterial pressure sensor upstream from the blood pump, and for a venous pressure sensor downstream from the hemotherapeutic unit.

In practical applications, it does occasionally happen that the blood tube forms a kink between the arterial blood pump and the dialyzer. One particularly endangered spot is directly before the inlet to the dialyzer. The kink formation leads to a constriction (stenosis) in the extracorporeal circulation circuit, where a substantial pressure difference builds up. The blood is forced at a high speed through the stenosis. The extremely large speed gradients can lead to shearing stresses that the erythrocytes are no longer able to withstand; the result is hemolysis. If a kink formation of this kind goes unnoticed for an extended period of time, the hemolysis can result in life-threatening health impairments.

It is true that the venous pressure sensor detects a complete closure of the blood tube, however, existing protective systems are only able to a limited extent to detect a constriction that is still partially permeable. A stenosis upstream from the hemotherapeutic unit does, in fact, lead to an increase in the pressure at the outlet of the blood pump, however, the conveying capacity of the latter remains virtually constant within a broad range. Thus, the pressure values do not change significantly at the arterial pressure sensor, nor at the venous pressure sensor. The latter depend essentially only on the delivery rate and the resistances to flow in the entry to and/or return from the patient.

One reliable method for detecting a kink location in the line system would be to introduce an additional pressure sensor at the outlet of the arterial blood pump. However, this approach would entail a considerably costlier effort with respect to the tubular systems. It would require additional connectors having hydrophobic filters, etc.

The German patent DE 199 01 078 describes a device for detecting stenoses during extracorporeal hemotherapy, which makes use of the arterial pressure sensor. The device is based on the principle of the blood pump generating an oscillating pressure signal that propagates across the tubular line system. In response to a serious enough stenosis between the blood pump and the hemotherapeutic unit, the pressure rises so markedly downstream from the blood pump that the occlusion of the pump rollers is partially removed. As a result, at times during the pumping operation, a little blood flows back upstream into the line system from the blood pump, causing an increase in the pulse amplitude measured at the arterial pressure sensor. At the same time, the generally negative arterial mean pressure approaches the zero line, since the delivery capacity abates.

In practice, however, the above method is only conditionally suited for detecting a beginning stenosis, since the occlusion of the pump does not subside until a delivery pressure of approximately 2 bar is attained. Until then, no significant change in the pressure signal is observed at the arterial pressure sensor. Nevertheless, the high pressure gradients at the stenosis can already lead to a dangerous hemolysis.

From the International Patent Application No. WO 97/10013, a method is known for detecting a stenosis at the entry to the patient, where an oscillating pressure signal, transmitted via the tubular line system, is analyzed. The pump signal that is attributed to the rotation of the blood pump is extracted from the pressure signal to facilitate detection of the patient's pulse signal, which is utilized for identifying the stenosis.

SUMMARY OF THE INVENTION

The object of the present invention is to provide a method for detecting stenoses, which is easily implemented in known hemotherapeutic devices, and which is distinguished by a high sensitivity such that stenoses may be detected before changes in the average value and amplitude of the arterial and venous pressure signal become discernible. It is also an object of the present invention to provide a device for detecting stenoses according to this method.

The method and the device of the present invention utilize the change in the dynamic performance of the tubular line system in response to the occurrence of a stenosis. The cause of the change in the dynamic performance is the compliance of the line system, i.e., the elastic yielding under pressure. This compliance is not regarded as a disturbance factor, rather, it is selectively utilized for detecting stenoses.

Based on the change in the dynamic performance, a stenosis that is beginning to form may be reliably detected, before the occlusion of the arterial blood pump is removed. One may make use of the tubular line systems (disposables) of the known hemotherapeutic devices, without the need for relying upon additional sensors or the like.

The method according to the present invention provides for an analysis of the frequency spectrum of the oscillating pressure signal. When a change in the frequency spectrum occurs, a stenosis is inferred. It is attributed to a change in the dynamic response of the tubular line system caused by the constriction.

For the method of the present invention, it is unimportant how the oscillating pressure signal is generated in the tubular line system. The volumetric blood pump, in particular the roller pump, which is used to deliver the blood in the arterial branch, has pressure pulses, which are preferably measured as oscillating signals.

The change in the dynamic response of the tubular line system results in a variable attenuation of the oscillating pressure signal. A stenosis leads to a heavy attenuation, particularly in response to higher frequencies.

An analysis, preferably a Fourier transform of the oscillating pressure signal, is carried out, and the attenuation of at least one harmonic component of the pressure signal is determined. From the change in the attenuation, the existence of a stenosis is then concluded. A stenosis may be reliably detected when only the attenuation of the first harmonic component is ascertained. However, the attenuation of one or of a plurality of harmonic component(s) of a higher order than the first harmonic component may also be determined. In principle, it is possible to infer a stenosis when an attenuation relating to only one harmonic component is present, or when an attenuation relating to a plurality of harmonic components is present. In this context, the known statistical methods may be utilized to further enhance sensitivity or reliability.

DETAILED DESCRIPTION

Figure 1:
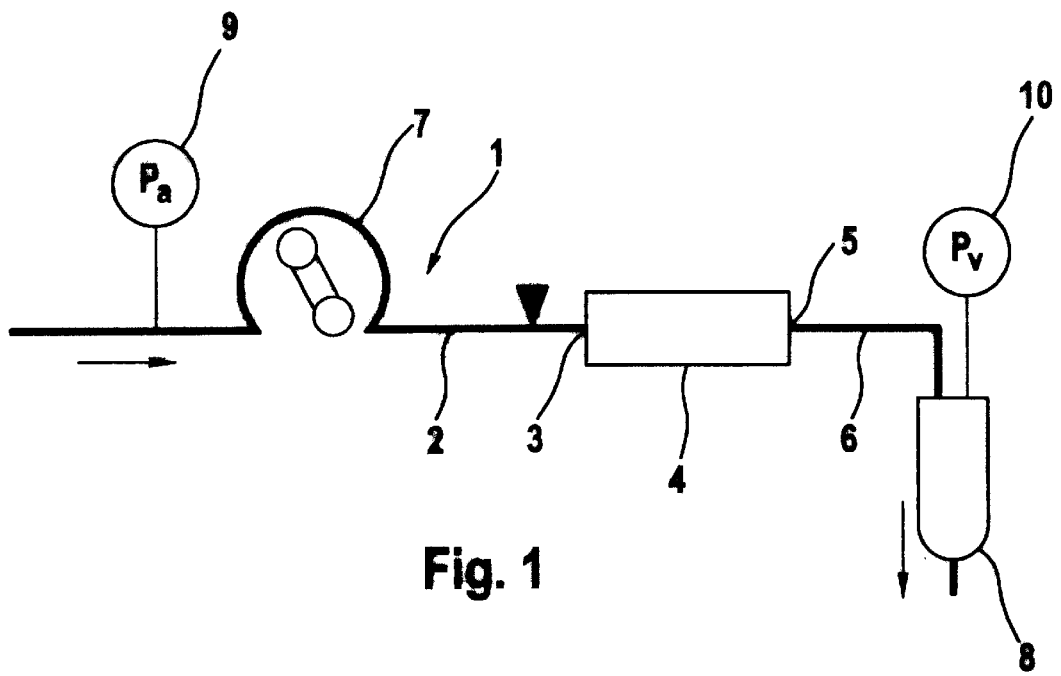
FIG. 1 shows a schematic representation of an extracorporeal blood-circulation circuit.

FIG. 1 illustrates the extracorporeal blood-circulation circuit in a schematic representation. The patient's blood flows through arterial branch 1 of a tubular line system 2 designed as a disposable system to inlet 3 of a hemotherapeutic unit 4, for example, a dialyzer. From outlet 5 of dialyzer 4, the blood flows through venous branch 6 of line system 2, back to the patient. The blood is delivered by a volumetric blood pump, in particular, a roller pump 7, which is connected upstream from dialyzer 4, into arterial branch 1 of line system 2. Connected to venous branch 6 of the line system is a drip chamber 8. The blood pressure in arterial branch 1, upstream from blood pump 7, is monitored by an arterial pressure sensor 9; and the pressure in venous branch 6, downstream from the dialyzer, is monitored by a venous pressure sensor 10. Dialyzer 4, tubular line system 2, blood pump 7, drip chamber 8, as well as pressure sensors 9 and 10 constitute an integral part of the known hemotherapeutic devices, for example, hemodialysis devices.

Figure 2:
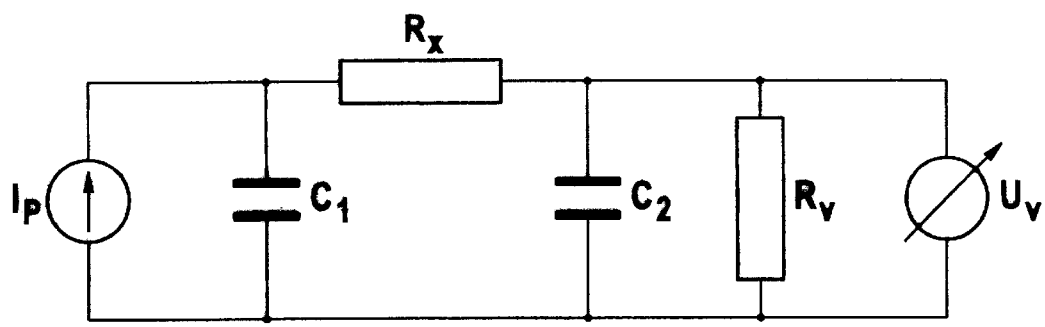
FIG. 2 shows an equivalent electrical circuit diagram of the extracorporeal blood-circulation circuit of FIG. 1.

During the extracorporeal hemotherapy, the pressure waves of blood pump 7 propagate as oscillating pressure signals across tubular line system 2. FIG. 2 depicts an equivalent electrical circuit diagram which may be used to describe the hydrodynamic properties of the line system.

The blood pump corresponds to a current source having impressed current $I_P$, the pressure of voltage $U_v$ measured at venous pressure sensor 10. The constriction formed by the squeezing action is represented by resistance $R_x$; the resistance to outward flow at the patient access, essentially caused by the venous needle, is represented by resistance $R_v$. $C_1$ and $C_2$ stand for the compliance, i.e., the elastic flexibility of the blood system before and after the constriction, respectively; $C_1$ is determined by the tubular system between the arterial pump, as well as the arterial drip chamber (not shown), which is configured between pump 7 and the dialyzer, and the constriction; $C_2$ is determined by the tubular system subsequent to the constriction, dialyzer 4 and venous drip chamber 8. An analysis of the complex transfer function (in the frequency space) of the above network, yields for a sinusoidal input signal $I_p$ having angular frequency $\omega$:

$$U_v = I_p \frac{R_v}{1 - \omega^2 R_x R_v C_1 C_2 + j\omega(R_x C_1 + R_v(C_1 + C_2))} \quad \text{(Equation 1)}$$

$I_P$ is a periodic signal whose period interval corresponds to half of the time of one revolution of a blood pump rotor having two symmetrically configured rollers. Therefore, one may calculate:

$$I_p = I_{P0} + I_{P1} e^{j\omega_P t} + I_{P2} e^{2j\omega_P t} + I_{P3} e^{3j\omega_P t} + \ldots$$

In this context, $I_{PO}$ is the continuous component of the pump flow, and $\omega_P$ is the fundamental frequency (first harmonic) of the blood pump (double rotational frequency). $I_{P1}$, $I_{P2}$, $I_{P3}$, etc., are the (complex) amplitudes of fundamental and harmonic waves. Due to the linearity of the network, it then holds for the output signal:

$$U_v = U_{V0} + U_{V1} e^{j\omega_P t} + U_{V2} e^{2j\omega_P t} + U_{V3} e^{3j\omega_P t} + \ldots$$

For the amounts of the amplitudes, it holds that:

$$U_{V0} = I_{P0} R_v \quad \text{(Equation 2)}$$

$$|U_{V1}| = |I_{P1}| \frac{R_v}{\sqrt{(1 - \omega_P^2 R_x R_v C_1 C_2)^2 + \omega_P^2 (R_x C_1 + R_v(C_1 + C_2))^2}}$$

$$|U_{V2}| = |I_{P2}| \frac{R_v}{\sqrt{(1 - 4\omega_P^2 R_x R_v C_1 C_2)^2 + 4\omega_P^2 (R_x C_1 + R_v(C_1 + C_2))^2}}$$

etc.

As previously mentioned, static component $U_{VO}$ is independent of the resistance of constriction $R_x$. For higher frequencies, the network functions as a $2^{nd}$ order low-pass filter. At this point, two special cases shall be considered: $R_x = 0$ and $R_v \ll R_x$.

In the case of $R_x = 0$, i.e., given no stenoses in the tubular system, it follows from equation 1 that:

$$U_V = I_P \frac{R_v}{1 - j\omega R_v(C_1 + C_2)} \quad \text{(Equation 3)}$$

This is the transfer function of a 1st order low-pass filter having critical frequency $\omega_g = 1(R_v(C_1 + C_2))$. Laboratory tests have shown that the harmonic waves of the blood pump, up to approximately the $3^{rd}$ order, are not observably attenuated by this low-pass filter, for as long as the tubular system does not have any stenoses. This means that the critical frequency of the low-pass filter must clearly lie above $3\omega_P$. Thus, it holds that:

$$\omega_P R_v(C_1 + C_2) \ll 1$$

This means that, in a first approximation, one may disregard the terms $\omega_P R_v C_1$ and $\omega_P R_v C_2$. Thus, for the case $R_V \ll R_x$, one obtains:

$$U_v = I_P \frac{R_v}{1 - j\omega R_x C_1} \quad \text{(Equation 4)}$$

Therefore, in response to an increasingly stronger kinking action, the blood system behaves in the manner of a low-pass filter having a critical frequency of $\omega_g = 1/(R_x C_1)$. The more vigorously the tube is kinked, the further the critical frequency falls, until it drops below the fundamental frequency of the blood pump. The higher harmonic components of the blood pump are attenuated to an even greater degree than the fundamental (first harmonic) component. Only the fundamental component is still observable. Considering the amount of the signal amplitudes, one derives from equation 4:

$$|U_v| = |I_P| \frac{R_v}{\sqrt{1 - \omega^2 R_x^2 C_1^2}}$$

$R_V$ may be determined from the static pressure signal (equation 2). Frequency $\omega$ of the blood pump, i.e., its harmonic components, is known from the spectrum. Therefore, it is possible to determine $R_x C_1$, so that a variable exists which is directly proportional to the magnitude of the squeezing of the tube. $C_1$ is the compliance of the blood system between the blood pump and the constriction, and is dependent upon its position, as well as upon the geometry and material of the tube. The more distant the kink is from the blood pump, the greater $C_1$ is. Thus, the method is especially sensitive to kinks in the vicinity of the dialyzer.

Figure 3:
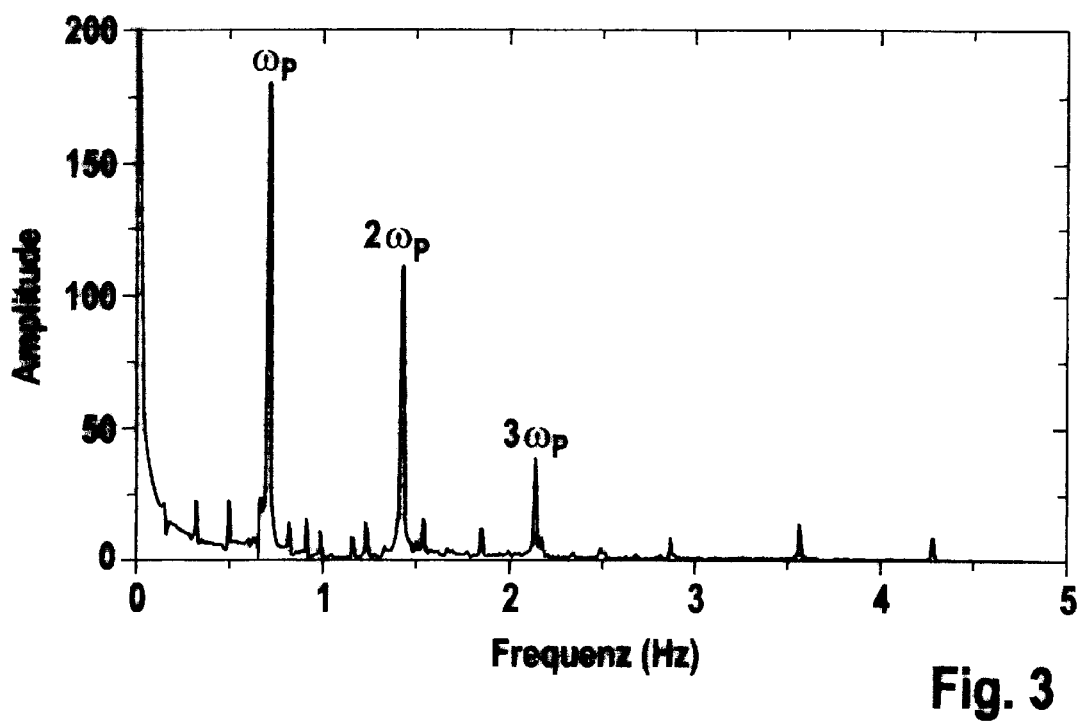
FIG. 3 shows the Fourier transform of the venous, oscillating pressure signal, without a stenosis being present.
Figure 4:
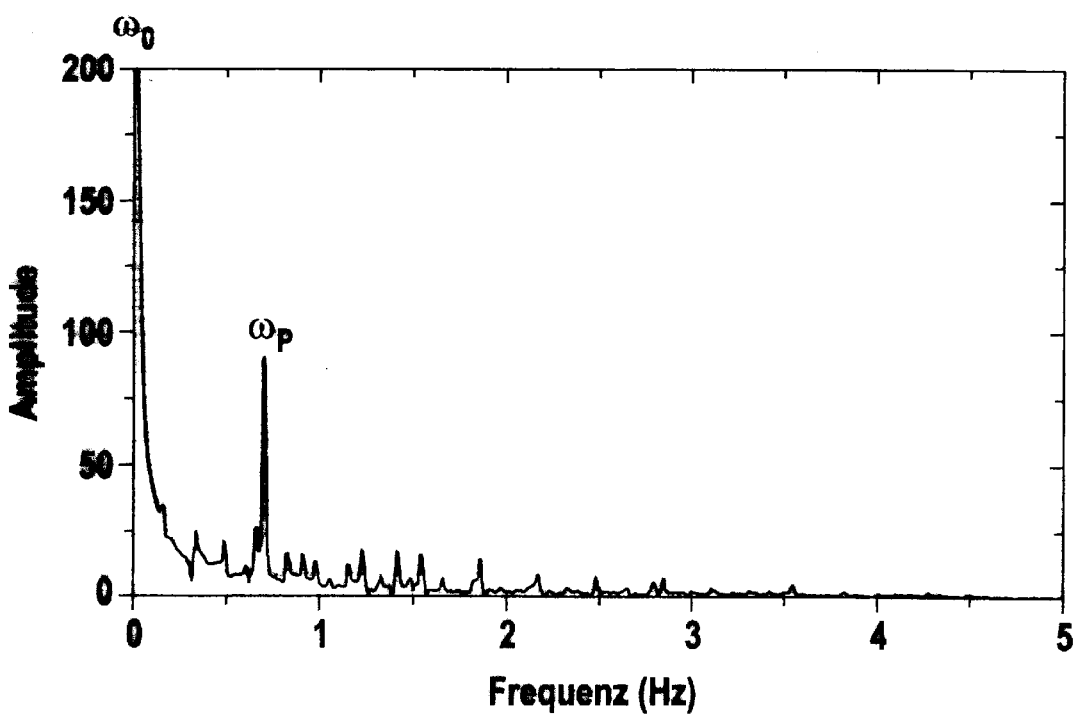
FIG. 4 shows the Fourier transform of the oscillating pressure signal, with a stenosis being present.

The method of the present invention for detecting stenoses is described as follows. The oscillating pressure signal in venous branch 6 of tubular line system 2 is measured by venous pressure sensor 10. A Fourier transform of the oscillating pressure signal is subsequently calculated. FIG. 3 shows the Fourier transform of the venous pressure signal having fundamental component $\omega_P$, as well as harmonic components $2\omega_P$, $3\omega_P$, etc., prior to the squeezing of arterial branch 1 of line system 2. FIG. 4 illustrates the Fourier transform of the pressure signal subsequent to the squeezing of arterial branch 1 between blood pump 7 and dialyzer 4. In FIG. 1, an arrow denotes the stenosis. It is clearly discernible that the amplitudes, in particular of harmonic components $2\omega_P$, $3\omega_P$, etc., are smaller. First harmonic component $2\omega_P$ and all higher-order harmonic components are hardly still discernible. Thus, as tests have shown, from the attenuation of the harmonic components, the existence of a stenosis may be concluded with certainty, even if it should happen that the fundamental component is not attenuated. In the process, a distinction may be clearly made between the kinking of the tube and an increased resistance to flow at the patient access, due, for example, to the rise in the blood's viscosity. Besides a stenosis, a blocking of the dialyzer may also be reliably detected using the method of the present invention. In this respect, the method of the present invention may also be employed to monitor the dialyzer.

Figure 5:
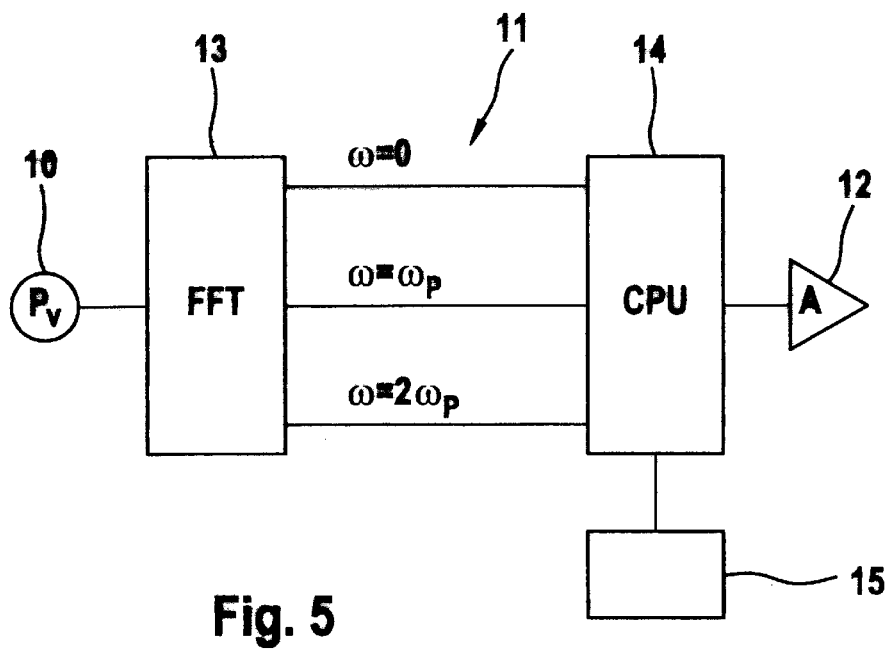
FIG. 5 shows a schematic representation of the essential components of a device for detecting stenoses.

FIG. 5 depicts an exemplary embodiment of the device of the present invention for detecting stenoses, which may be a separate subassembly or a component of the known hemotherapeutic devices.

The device has a venous pressure sensor 10 for measuring the oscillating pressure signal in venous branch 6 of tubular line system 2 of the extracorporeal blood-circulation circuit of the hemotherapeutic device. Venous pressure sensor 10 is generally a component of the known hemotherapeutic devices (see FIG. 1). Moreover, the device has means 11 for analyzing the pressure signal measured by pressure sensor 10, as well as an alarm device 12. Means 11 for analyzing the pressure signal include means 13 for calculating a Fourier transform FFT and a central processing unit CPU 14 for analyzing the frequency spectrum of the pressure signal. Also provided is a memory unit 15.

From the Fourier spectrum of the pressure signal, one extracts the static component ($\omega=0$), the blood pump's fundamental frequency ($\omega_P$), and the first harmonic component ($\omega=2\omega_P$). At the beginning of the hemotherapy, the amplitude of the first harmonic component is input as a reference value into memory unit 15. In so doing, the assumption is made that no stenosis exists. Alternatively, however, a reference value ascertained in comparative tests may also be preset for the first harmonic component. During the hemotherapy, the first harmonic component is continuously extracted from the Fourier spectrum. CPU 14 has means for generating a difference between the reference value and the extracted value of the amplitude. This difference is compared to a predefined threshold value. If the difference is greater than the threshold value, then CPU 14 transmits an alarm signal to alarm device 12. At this point, alarm device 12 produces an optical and/or acoustical alarm, since a stenosis is present.

To enhance security and increase sensitivity, the frequency spectrum may also be analyzed on the basis of further harmonic components of a higher order. For each harmonic component, a reference value is then stored in memory unit 15. CPU 14 generates the difference between each reference value and the corresponding amplitude of the harmonic component. CPU 14 generates the alarm signal when, for at least one harmonic component, the difference is greater than a predefined threshold value.

Figure 6:
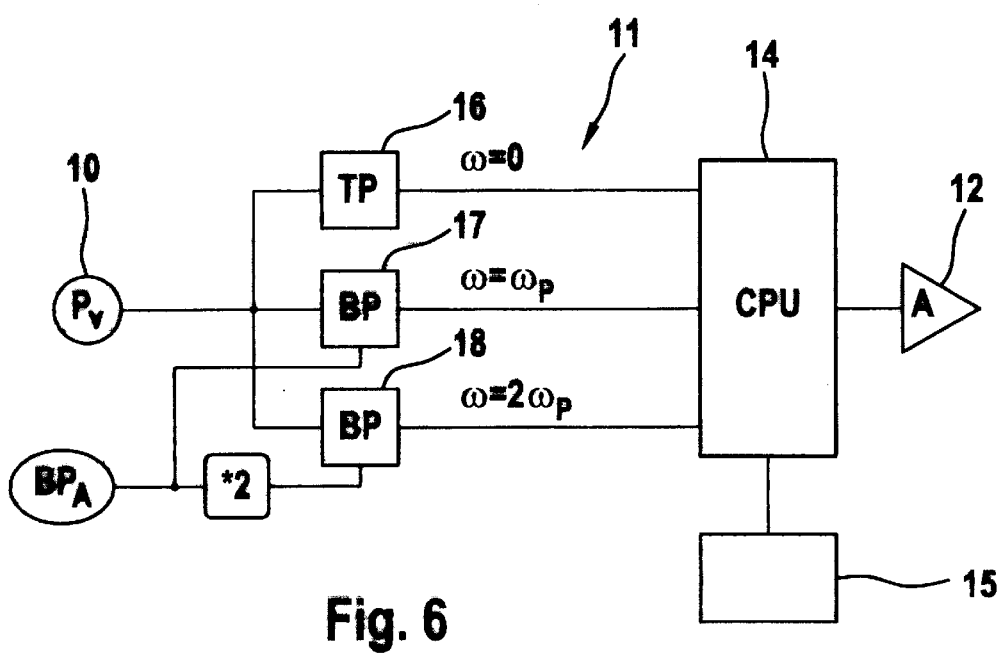
FIG. 6 shows a further specific embodiment of the device for detecting stenoses.

FIG. 6 shows another exemplary embodiment of the device of the present invention for detecting stenoses, which differs from the embodiment depicted in FIG. 5 by the means for implementing the Fourier transform. Equivalent parts are denoted by the same reference numerals in these figures.

To extract the static component, the blood pump's fundamental frequency, and the first harmonic component, the specific embodiment of FIG. 6 has a low-pass filter 16, as well as two variable-frequency band-pass filters 17 and 18, which each constitute a lock-in amplifier. Low-pass filter 16 filters out the time-averaged signal ($\omega=0$). Arterial blood-pump signal $BP_A$ is used as a frequency basis for first band-pass filter 17, while the blood-pump signal multiplied by factor 2 is used as a frequency basis for second band-pass filter 18. Arterial blood pump signal $BP_A$ is a signal that is correlated to the rotational speed of the blood pump. In the case of a roller pump having two rollers, for example, the frequency of the blood-pump signal is twice the rotation of the pump rotor. This signal may be tapped off, for example, at the pump control or at a separate tachometer.

First band-pass filter 17 extracts the blood pump's fundamental frequency, and the second band-pass filter extracts the first harmonic component. Apart from that, the devices according to FIGS. 5 and 6 have equivalent designs.

We claim:

1. A method for detecting stenoses in a tubular line system during an extracorporeal hemotherapy, said method comprising:

generating an oscillating pressure signal in the tubular line system, wherein the tubular line system comprises an arterial branch going out from a patient and leading to a hemotherapeutic unit, and a venous branch going out from the hemotherapeutic unit and leading to the patient;

measuring the oscillating pressure signal, wherein the oscillating pressure signal includes a frequency spectrum comprising a fundamental component and at least one harmonic component;

analyzing the oscillating pressure signal by analyzing the frequency spectrum, wherein analyzing the frequency spectrum comprises determining an attenuation of at least one of the at least one harmonic component; and determining whether a stenosis exists based upon a change in the attenuation.

2. The method of claim 1, wherein the attenuation of at least one of the at least one harmonic component comprises at least one of an attenuation of the first harmonic component, an attenuation of one higher-order harmonic component, and an attenuation of a plurality of higher-order harmonic components.

3. The method of claim 1, wherein analyzing the oscillating pressure signal comprises calculating a Fourier transform of the oscillating pressure signal.

4. The method of claim 3, wherein calculating a Fourier transform of the oscillating pressure signal is achieved by a low-pass filter and two variable-frequency band-pass filters.

5. The method of claim 1, wherein determining whether a stenosis exists comprises calculating a difference between the amplitude of a harmonic component ascertained at the beginning of the extracorporeal hemotherapy and the amplitude of the harmonic component ascertained during the extracorporeal hemotherapy, and concluding that a stenosis exists when the difference is greater than a predefined threshold value.

6. The method of claim 1, wherein the tubular line system further comprises a volumetric blood pump located in the arterial branch, wherein the volumetric blood pump comprises a roller pump which delivers the patient's blood into the arterial branch and which has a pressure pulse, and wherein measuring the oscillating pressure signal comprises measuring the pressure pulse.

7. The method of claim 1, wherein the tubular line system further comprises a pressure sensor located in the venous branch, downstream from the hemotherapeutic unit, wherein the pressure sensor measures the oscillating pressure signal.

8. A device for detecting stenoses in a tubular line system during an extracorporeal hemotherapy, said device comprising:

an arterial branch going out from a patient and leading to a hemotherapeutic unit;

a venous branch going out from the hemotherapeutic unit and leading to the patient;

means for generating an oscillating pressure signal in the tubular line system, wherein the oscillating pressure signal includes a frequency spectrum comprising a fundamental component and at least one harmonic component;

means for measuring the oscillating pressure signal; and means for analyzing the oscillating pressure signal including means for analyzing the frequency spectrum and means for determining an attenuation of at least one of the at least one harmonic component.

9. The device of claim 8, wherein the attenuation of at least one of the at least one harmonic component comprises at least one of an attenuation of the first harmonic component, an attenuation of one higher-order harmonic component, and an attenuation of a plurality of higher-order harmonic components.

10. The device of claim 9, wherein the means for generating an oscillating pressure signal comprise a volumetric blood pump.

11. The device of claim 10, wherein the volumetric blood pump comprises a roller pump.

12. The device of claim 9, wherein the means for measuring the oscillating pressure signal include a venous pressure sensor which is located in the venous branch downstream from the hemotherapeutic unit.

13. The device of claim 8, wherein the means for analyzing the oscillating pressure signal further include means for calculating a Fourier transform.

14. The device of claim 13, wherein the means for calculating a Fourier transform include a low-pass filter and two variable-frequency band-pass filters.

15. The device of claim 8, wherein the means for analyzing the oscillating pressure signal further include means for calculating a difference between the amplitude of a harmonic component ascertained at the beginning of the extracorporeal hemotherapy and the amplitude of the harmonic component ascertained during the extracorporeal hemotherapy, wherein a stenosis is concluded to exist when the difference is greater than a predefined threshold value.

16. The device of claim 8, wherein the means for generating an oscillating pressure signal comprise a volumetric blood pump.

17. The device of claim 16, wherein the volumetric blood pump comprises a roller pump.

18. The device of claim 8, wherein the means for measuring the oscillating pressure signal include a venous pressure sensor which is located in the venous branch downstream from the hemotherapeutic unit.

* * * * *